United States Patent
Zhou et al.

(10) Patent No.: US 9,686,540 B2
(45) Date of Patent: Jun. 20, 2017

(54) ROBUST COLORIMETRIC PROCESSING METHOD FOR PAPER BASED SENSORS

(71) Applicant: Xerox Corporation, Norwalk, CT (US)

(72) Inventors: Jing Zhou, Webster, NY (US); Nancy Y. Jia, Webster, NY (US); Wei Hong, Amherst, MA (US); Mandakini Kanungo, Webster, NY (US); Xing Liu, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 175 days.

(21) Appl. No.: 14/799,969

(22) Filed: Jul. 15, 2015

(65) Prior Publication Data

US 2016/0057413 A1 Feb. 25, 2016

Related U.S. Application Data

(60) Provisional application No. 62/041,181, filed on Aug. 25, 2014.

(51) Int. Cl.
*H04N 17/02* (2006.01)
*G01N 21/25* (2006.01)
(Continued)

(52) U.S. Cl.
CPC .......... *H04N 17/02* (2013.01); *G01N 21/253* (2013.01); *G01N 21/78* (2013.01); *G01N 21/8483* (2013.01); *G06K 9/4652* (2013.01); *G06K 9/6201* (2013.01); *G06T 7/90* (2017.01); *G01N 21/274* (2013.01); *G01N 2021/7759* (2013.01);
(Continued)

(58) Field of Classification Search
CPC ...... H04N 17/02; G06T 7/90; G01N 21/8483; G01N 21/253; G01N 21/78; G01N 21/274; G01N 2021/7759; G01N 2201/0461; G06K 9/4652; G06K 9/6201; G06K 2009/4666

See application file for complete search history.

(56) References Cited

U.S. PATENT DOCUMENTS 2,712,508 A 7/1955 Massey
3,145,118 A 8/1964 Mahoney
(Continued)

FOREIGN PATENT DOCUMENTS

GB 1 050 651 12/1966
WO WO 2007/050539 5/2007
(Continued)

OTHER PUBLICATIONS

Allen Wyatt: Printing a Document's Mirror Image, Allen Wyatt's WORDTIPS menu interface; Nov. 5, 2014; 3 pages; http://word.tips.net/T001475_Printing_a_Documtents_Mirror_Image.html.
(Continued)

*Primary Examiner* — Christopher S Kelley
*Assistant Examiner* — Nasim Nirjhar
(74) *Attorney, Agent, or Firm* — Fay Sharpe LLP

(57) ABSTRACT

The present disclosure proposes a colorimetric method that couples sensor design with image processing to enable automated evaluation of test results obtained by paper-based sensors. The proposed method can match ink color and dye used in colorimetric reaction in terms of their absorption in spectral range (e.g., red, green, blue). A near-zero absorption channel can then be used to normalize absorption channels and construct a composite image.

21 Claims, 10 Drawing Sheets

(51) Int. Cl.
*G06K 9/46* (2006.01)
*G06K 9/62* (2006.01)
*G01N 21/78* (2006.01)
*G01N 21/84* (2006.01)
*G06T 7/90* (2017.01)
*G01N 21/77* (2006.01)
*G01N 21/27* (2006.01)

(52) U.S. Cl.
CPC .......... *G01N 2201/0461* (2013.01); *G06K 2009/4666* (2013.01)

(56) References Cited

U.S. PATENT DOCUMENTS

| | | |
|---|---|---|
| 3,826,573 A | 7/1974 | Heinzer |
| 3,982,056 A | 9/1976 | Holder, Jr. |
| 4,160,646 A | 7/1979 | Furutani et al. |
| 4,606,264 A | 8/1986 | Agronin et al. |
| 5,055,884 A | 10/1991 | Ndebi et al. |
| 5,317,127 A | 5/1994 | Brewster, Jr. et al. |
| 5,614,933 A | 3/1997 | Hindman et al. |
| 5,820,284 A | 10/1998 | Owada et al. |
| 5,891,228 A | 4/1999 | Baker et al. |
| 6,092,578 A | 7/2000 | Machida et al. |
| 6,196,675 B1 | 3/2001 | Deily et al. |
| 6,458,867 B1 | 10/2002 | Wang et al. |
| 6,723,500 B2 | 4/2004 | Yu |
| 7,267,938 B2 | 9/2007 | Anderson et al. |
| 7,454,880 B1 | 11/2008 | Austin et al. |
| 7,969,624 B2 | 6/2011 | Mestha et al. |
| 8,249,879 B2 | 8/2012 | Bangalore et al. |
| 8,377,710 B2 | 2/2013 | Whitesides et al. |
| 8,574,924 B2 | 11/2013 | Sia et al. |
| 8,603,832 B2 | 12/2013 | Whitesides et al. |
| 8,627,867 B2 | 1/2014 | Lahood et al. |
| 8,628,729 B2 | 1/2014 | Carrilho et al. |
| 8,730,460 B2 | 5/2014 | Yan et al. |
| 8,821,810 B2 | 9/2014 | Whitesides et al. |
| 2001/0041222 A1 | 11/2001 | Gilfert et al. |
| 2002/0098124 A1 | 7/2002 | Bentsen et al. |
| 2004/0086424 A1 | 5/2004 | Schembri |
| 2004/0179053 A1 | 9/2004 | Itoh |
| 2005/0111861 A1 | 5/2005 | Calamita et al. |
| 2007/0059718 A1 | 3/2007 | Toner et al. |
| 2007/0061393 A1 | 3/2007 | Moore |
| 2010/0145491 A1 | 6/2010 | Troian |
| 2010/0247197 A1 | 9/2010 | Okamoto et al. |
| 2011/0111517 A1 | 5/2011 | Siegel et al. |
| 2011/0123398 A1 | 5/2011 | Carrilho et al. |
| 2011/0292142 A1 | 12/2011 | LeFevre et al. |
| 2012/0053930 A1 | 3/2012 | Bangalore et al. |
| 2012/0181184 A1 | 7/2012 | Whitesides et al. |
| 2012/0198684 A1 | 8/2012 | Carrilho et al. |
| 2012/0198685 A1 | 8/2012 | Bernardina Junior |
| 2012/0257188 A1* | 10/2012 | Yan .............. G01N 33/49 356/40 |
| 2012/0328905 A1 | 12/2012 | Guo et al. |
| 2013/0034869 A1 | 2/2013 | Whitesides et al. |
| 2013/0084630 A1* | 4/2013 | Rolland ............ G01N 21/78 435/287.8 |
| 2013/0096392 A1* | 4/2013 | Adams ............ A61B 5/0075 600/301 |
| 2013/0162702 A1 | 6/2013 | Tombs et al. |
| 2014/0101956 A1 | 4/2014 | Priebe et al. |
| 2014/0261964 A1 | 9/2014 | Barss et al. |
| 2014/0295472 A1* | 10/2014 | Shevkoplyas ...... G01N 33/526 435/13 |
| 2015/0211987 A1* | 7/2015 | Burg ............ G01N 35/00029 356/402 |
| 2015/0281492 A1* | 10/2015 | Mamura ........... H04N 1/00779 358/1.15 |

FOREIGN PATENT DOCUMENTS

| | | |
|---|---|---|
| WO | WO 2011/000047 | 1/2011 |
| WO | WO 2013/010178 | 1/2013 |
| WO | WO 2013/116831 | 8/2013 |
| WO | WO 2014/113770 | 7/2014 |

OTHER PUBLICATIONS

Bracher et al.; Patterned Paper as a template for the delivery of reactants in the fabrication of planar materials; The Royal Society of Chemistry Journal; *Soft Matter*, Sep. 21, 2010; 6(18): 4303-4309; Previously Presented 1-16.

Martinez et al.; Diagnostics for the Developing World: Microfluidic Paper-Based Analytical Devices; Analytical Chemistry; Jan. 1, 2010; pp. 3-10; vol. 82, Issue No. 1; American Chemical Society.

Extended European Search Report of European Application No. 15181307.8-1554 / 2990782 dated Apr. 18, 2016.

* cited by examiner

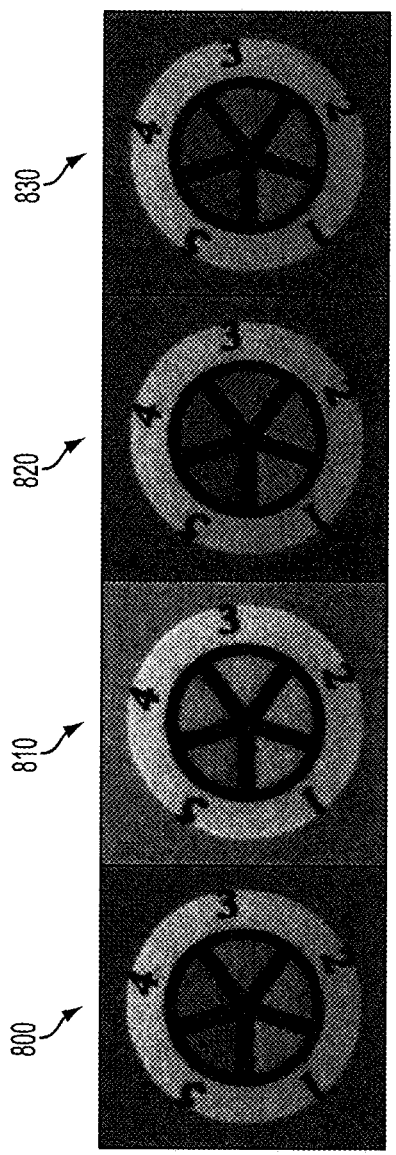

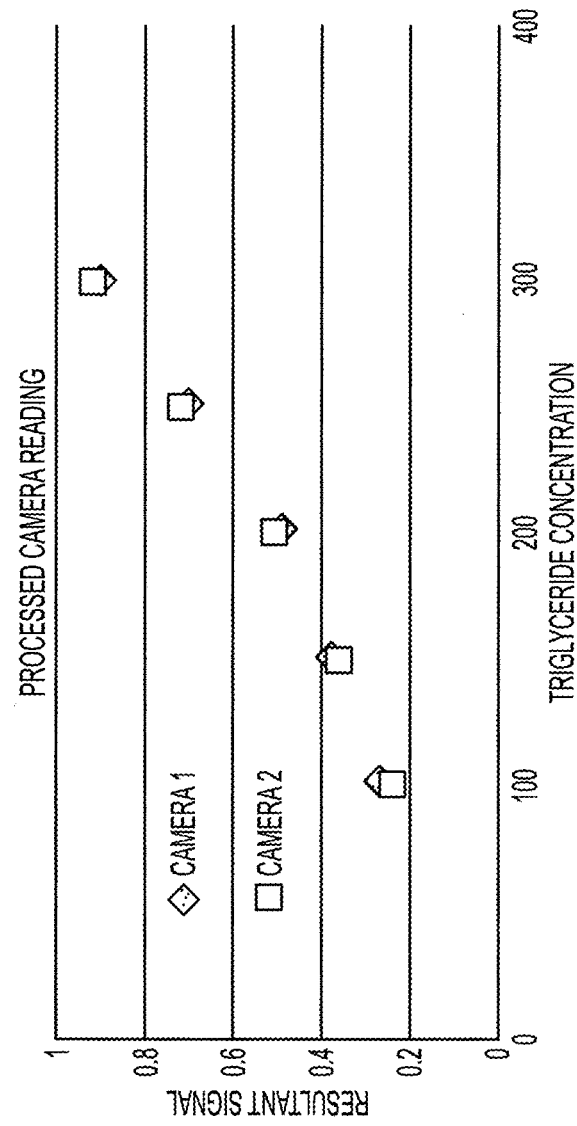

ROBUST COLORIMETRIC PROCESSING METHOD FOR PAPER BASED SENSORS

This application claims priority to U.S. Provisional Patent Application No. 62/041,181, filed Aug. 25, 2014, by Jing Zhou et al. and entitled "ROBUST COLORIMETRIC PROCESSING METHOD FOR PAPER-BASED SENSORS" and is incorporated herein by reference in its entirety.

CROSS REFERENCE TO RELATED PATENTS AND APPLICATIONS

U.S. Provisional Patent Application No. 62/041,174, filed Aug. 25, 2014, by Hong et al., and entitled "DESIGN OF PAPER SENSOR";

U.S. Provisional Patent Application No. 62/041,191, filed Aug. 25, 2014, by Jia et al., and entitled "PAPER SENSING AND ANALYTIC SERVICE WORKFLOW METHODS AND SYSTEMS";

U.S. patent application Ser. No. 14/312,061, filed Jun. 23, 2014, by Zhou et al., and entitled "APPARATUS FOR FORMING HYDROPHOBIC STRUCTURES IN POROUS SUBSTRATES";

U.S. patent application Ser. No. 14/312,209, filed Jun. 23, 2014, by Zhou et al., and entitled "APPARATUS FOR PRODUCING PAPER-BASED CHEMICAL ASSAY DEVICES";

U.S. patent application Ser. No. 14/311,970, filed Jun. 23, 2014, by Beachner et al., and entitled "SYSTEM AND METHOD FOR FORMING BONDED SUBSTRATES"; and U.S. patent application Ser. No. 14/311,909, filed Jun. 23, 2014, by O'Neil et al., and entitled "SYSTEM AND METHOD FOR FORMING HYDROPHOBIC STRUCTURES IN A POROUS SUBSTRATE", are incorporated herein by reference in their entirety.

BACKGROUND

Paper-based sensing (i.e. paper based test devices) is an emerging technology that has advantages relative to traditional test strips in terms of cost and multiplexing. The concern of poor accuracy on paper-based sensors and paper test strips, due to the colorimetric measurement, has limited them from quantitative applications. In existing test strip applications, a user has to manually compare resultant colors to a set of colors on a reference card. This is neither user friendly nor reliable. Recently some companies have developed phone 'apps' to automate the test strip reading process using a phone camera.

INCORPORATION BY REFERENCE

U.S. Pat. No. 8,377,710, issued Feb. 19, 2013, by Whitesides et al., and entitled "LATERAL FLOW AND FLOW-THROUGH BIOASSAY DEVICES BASED ON PATTERNED POROUS MEDIA, METHODS OF MAKING SAME, AND METHODS OF USING SAME";

U.S. Patent Application Publication No. 2011/0111517, published May 12, 2011, by Siegel et al., and entitled "PAPER-BASED MICROFLUIDIC SYSTEMS";

U.S. Patent Application Publication No. 2011/0123398, published May 26, 2011, by Carrilho et al., and entitled "THREE-DIMENSIONAL MICROFLUIDIC DEVICES";

U.S. Patent Application Publication No. 2012/0053930, published Mar. 1, 2012, by Bangalore et al., and entitled "SYSTEM AND METHOD OF PROVIDING A SPOKEN DIALOG INTERFACE TO A WEBSITE";

U.S. Patent Application Publication No. 2012/0181184, published Jul. 19, 2011, by Whitesides et al., and entitled "MICROFLUIDIC, ELECTROCHEMICAL DEVICES";

U.S. Patent Application Publication No. 2012/0198685, published Aug. 9, 2012, by Bernardina Junior, and entitled "METHOD TO PRODUCE AN ELECTRODE WITH A LOW LEVEL OF HYDROGEN AND LOW ABSORPTION OF MOISTURE";

U.S. Patent Application Publication No. 2012/0257188, published Oct. 11, 2012, by Yan et al., and entitled "PAPER BASED SPECTROPHOTOMETRIC DETECTION OF BLOOD HEMOGLOBIN CONCENTRATION";

U.S. Patent Application Publication No. 2013/0034869, published Feb. 7, 2013, by Whitesides et al., and entitled "DEVICES AND METHODS FOR MULTIPLEXED ASSAYS"; and U.S. Patent Application Publication No. 2013/0084630, published Apr. 4, 2013, by Rolland et al., and entitled "QUANTITATIVE MICROFLUIDIC DEVICES", are incorporated herein by reference in their entirety.

BRIEF DESCRIPTION

The present disclosure provides for a colorimetric processing method for paper based sensors comprising: taking a picture of a colorimetric paper sensor for colorimetric reactions; identifying the type of paper sensor by image processing; identifying one color channel in which both a dye and reference color have near zero absorption and wherein the color channels in which both dye and the reference color have absorption; identifying the known absorption ratio between the dye and the reference color in each color channel; separating each test area in the channel from the non-test areas; normalizing each absorption channel by the near zero absorption channel to remove spatial variation; calibrating the test area reading with the reference color and a substrate white in the composite image; and, reporting the concentration of a test substance analyte based on the calibrated reading in each test area.

The present disclosure further provides for colorimetric processing method for paper based sensors comprising: using a camera and taking a picture of a colorimetric paper sensor for colorimetric reactions; identifying the type of paper sensor by image processing; identifying one color channel in which both a dye and reference color have near zero absorption and wherein the color channels in which both the dye and the reference color have absorption; identifying the known absorption ratio between the dye and the reference color in each color channel; separating each test area in the channel from the non-test areas; and, normalizing each absorption channel by the near zero absorption channel to remove spatial variation. The colorimetric paper sensor is a biomedical paper sensor. The paper sensor includes a plurality of axially radiating test zones, wherein each of the axially radiating test zones are divided by wax ink barrier walls. Each of the axially radiating test zones can contain a unique test reagent therein. A reference region surrounds the plurality of axially radiating test zones, wherein the reference region includes a calibration color area, including a predeterminable color for comparing to one or more of the axially radiating test zones.

The present disclosure further provides for a colorimetric processing method for paper based sensors comprising: taking a picture of a colorimetric paper sensor for colorimetric reactions; identifying the type of paper sensor by image processing; identifying one color channel in which both a dye and reference color have near zero absorption and wherein the color channels in which both the dye and the reference color have absorption; identifying the known absorption ratio between the dye and the reference color in each color channel; separating each test area in the channel from the non-test areas; and, normalizing each absorption channel by the near zero absorption channel to remove spatial variation. The colorimetric paper sensor is a biomedical paper sensor. The paper sensor can include a plurality of axially radiating test zones, wherein each of the axially radiating test zones are divided by wax ink barrier walls. Each of the axially radiating test zones can contain a unique test reagent therein. A reference region can surround the plurality of axially radiating test zones. A total device area can include the combined areas of a reference region area and the axially radiating test zones area. The axially radiating test zones area can be at least 37.5% of the total device area. The reference region area further includes a substrate region separating the axially radiating test zones area and the calibration color area.

The present disclosure still further provides for a colorimetric processing method for paper based sensors comprising: taking a picture of a colorimetric paper sensor for colorimetric reactions; identifying the type of paper sensor by image processing; identifying one color channel in which both a dye and reference color have near zero absorption and wherein the color channels in which both the dye and the reference color have absorption; identifying the known absorption ratio between the dye and the reference color in each color channel; separating each test area in the channel from the non-test areas; and, normalizing each absorption channel by the near zero absorption channel to remove spatial variation. The colorimetric paper sensor is a biomedical paper sensor.

BRIEF DESCRIPTION OF THE DRAWINGS

FIG. 11 is the same sensor image, as shown in FIG. 8, from another or second phone camera;

FIG. 12 is a graph of resultant signals relative to triglyceride concentrations plotting processed camera readings from the first phone camera and the second phone camera.

DETAILED DESCRIPTION

Figure 1:
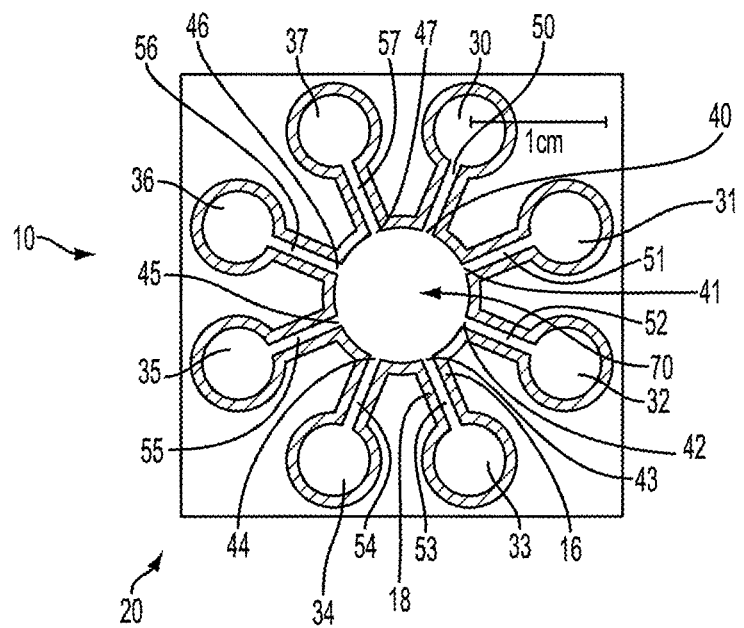
FIG. 1 represents one type of a paper based sensor or test device.
Figure 2:
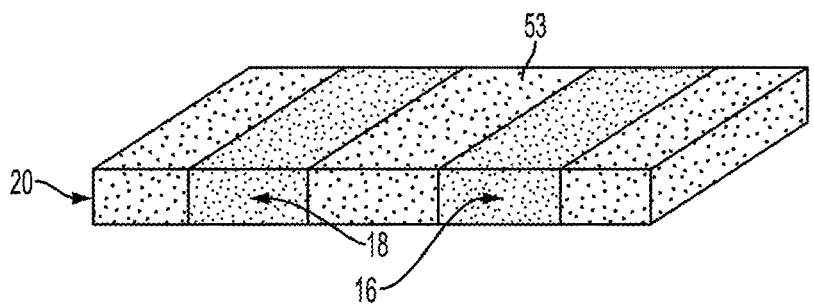
FIG. 2 represents an enlarged partial section of the paper-based sensor of FIG. 1.

A paper-based sensor or paper-based test device 10, as shown in FIGS. 1 and 2, is a small biomedical device made of paper, wax, and reagents that can analyze bioassays in test fluids or test liquids such as blood, urine and saliva. The hydrophobic barrier walls 16, 18 are made of wax that penetrates through the entire thickness of the paper 20 (i.e. hydrophilic matrix) to create and separate (i.e. divide) various fluidic components such as a series of test regions 30, 31, 32, 33, 34, 35, 36, 37, fluid entrances 40, 41, 42, 43, 44, 45, 46, 47, transport channels 50, 51, 52, 53, 54, 55, 56, 57, and mixers or reagents. The transport channels 50-57, can be hydrophobic (i.e. wax) channels extending through the hydrophilic matrix paper 20. Various reagents with various and/or different concentrations can be pre-deposited on the test regions 30-37. During the diagnostic process, capillary forces pull portions of the test fluid 70 to associated multiple test regions 30-37 and upon contacting the pre-deposited reagents, react with the respective portions of test fluid 70. A signal, color change, or color shade is generated if a specific analyte is present in the test fluid 70; for instance, a color shade or change develops where the color density varies as a result of the concentration of the analyte. The color change or shade can be captured and recorded by an imaging device such as a smart phone or camera phone and can then be processed by an algorithm to calculate the concentration of each analyte based on a calibration curve or color scale of the device. The diagnostic results and/or raw data (if the image processing and diagnostic analysis is done on the server side) can be uploaded to a data server where the user's or patient's history can be stored for inquiry and advanced data analytics can be performed which can help to detect and prevent adverse health conditions/diseases. It is to be appreciated that the user's data analytics or predictive analytics can be used for trend monitoring, health screening, risk assessment, et al.; the results of which can include non-adverse health conditions.

Paper based sensors have several advantages over traditional test strips. Test strips are simplex (one test per strip), while paper sensors can be multiplex (multiple tests on one device). Traditional test strips require relatively more test fluid than paper sensors. Test strips are fabricated by analog technology, while paper sensors can be digitally printed and quantitatively analyzed which enables greater customization and personalization.

Use of paper based sensors is an emerging technology that provides advantages over traditional test strips in terms of cost and multiplexing. The current paper based sensors require a user to provide a certain amount of test liquid (blood, urine, etc.) to ensure the accuracy of the test. The level of multiplexing is typically limited by the printing resolution and straightness of printed wax vertical walls/barriers. Additionally, the current method of reading colorimetric information uses either a separate manual reference card or uses a mobile application available in the market that can suffer from the variability for individual reading devices (camera, illumination, light conditions, surrounding light conditions, etc.). It is important to come up with novel designs for the paper based sensor that can achieve a higher level of multiplexing than the current devices available in the market, and can provide higher readout accuracy regardless of the variation from individual reading devices.

The present disclosure (referring to FIGS. 3-7) provides for a design and construction of paper sensors or test devices 100 that have an increased total test area relative to an overall fixed device area. This novel design and construction increases the extent of multiplexing and improves the readout accuracy. The present disclosure provides for a device 100 that includes several unique features. The resolution of the wax barriers are high so that the device can achieve higher levels of multiplexing and can include larger overall test area, relative to the overall device area, for increased read out accuracy. A reference region, including a calibration color area, can be directly printed on the paper sensor for direct side-by-side comparison to the corresponding colorimetric reactions in respective test regions. This can eliminate the use of a separate reference card, which has been theretofore necessary for 'reading' and interpreting paper based sensors.

Prior art paper based sensors 10 (FIGS. 1-2) are typically made through a manual oven process. The wax in hydrophobic channels 50-57 needs to spread more laterally (reflow) to achieve a total penetration through the paper. As a result, the size of the test areas 30-37 and the level of multiplexing are limited relative to an overall fixed device size due to the non-uniformity/large channel variation caused by uncontrolled reflow of wax. In contrast, the device fabricated using the controlled process described in U.S. patent application Ser. No. 14/311,909, filed Jun. 23, 2014, by O'Neil et al., and entitled "SYSTEM AND METHOD FOR FORMING HYDROPHOBIC STRUCTURES IN A POROUS SUBSTRATE" (incorporated herein by reference), has a higher resolution and outstanding channel uniformity. These advantages enable the paper based sensor to achieve the design and construction as described hereinafter.

Figure 3:
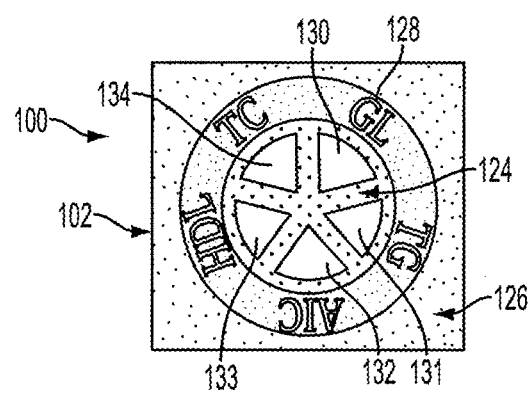
FIG. 3 shows a top elevational view of an exemplary paper-based test device including a reference calibration color area, a plurality of test zones, a plurality of ink barriers, and a label area.
Figure 4:
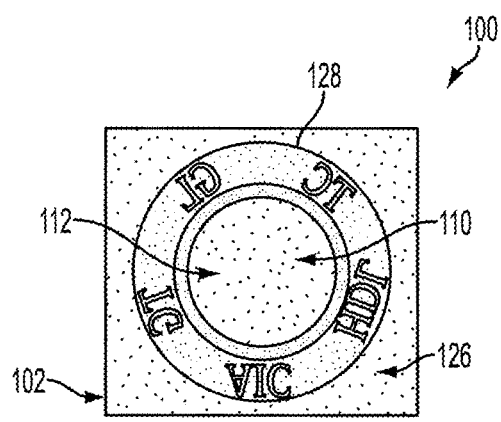
FIG. 4 shows a bottom elevational view of an exemplary paper-based test device shown in FIG. 3.

Referring now to FIGS. 3 and 4, some of the features of the paper-based sensor 100 disclosed herein include: larger test area 110, including segmented test zones 130, 131, 132, 133, 134, relative to an overall fixed size device area 102 compared to prior art sensors; and, fully utilized plasma separation membrane layer 112 on the backside of the device for improved separation of plasma from the blood. The paper-based sensor 100 can include a channel structural area 124 which increases the readout accuracy and level of multiplexing without requiring a larger test sample (i.e. blood). A reference or calibration reference color area 126 can include a distinct area and can be directly printed on the device either as part of the channel structure or as an additional pattern. An auxiliary information area 128 can surround the test area 110.

In another exemplary embodiment (FIG. 5), a paper sensor device 200 can include the following components: a structural forming layer 216, an optional filter membrane layer 212, and at least two laminating layers 218, 220. The structure forming layer 216 can include a channel structural area 224, a test area 210, a calibration reference area 226, and auxiliary information area 228.

The test zone or test area 210 can include 1 to n (n>=2) individual segmented test zones 230, 231, 232, 233, 234, 235. The segmented test zones 230-235 can be arranged in an axially symmetric or axially radiating manner. The total test area 210 is from about 25% to about 60%, and preferably at least 37.5% of the total device area 202. The minimum area of individual test zones 230-235 can be about 5 mm². Comparing to the prior art devices (FIG. 1), the individual test zones 230-235, of the present disclosure, are at least three (3) times larger. Test zones 230-235 are surrounded and divided by wax ink barrier walls 236, 237, 238, 239, 240, 241 (i.e. solid ink barriers) with a wall width of about 100 um for maximizing the area of the test regions or zones 230-235 relative to a limited space or area for the device 202. It is to be appreciated that a majority of the volume of a test sample is utilized and reaches, i.e. reacts with, the reagents in each of the test zones 230-235.

One exemplary test panel can include respective reagents in test zones 230-235 for measuring levels of triglyceride, total cholesterol, HDL (i.e. three individual test zones). Another exemplary test panel can include respective reagents in test zones for measuring lipid panel, i.e. levels of triglyceride, total cholesterol, HDL, Hemoglobin A1C (HbA1C), glucose (i.e. five individual test zones). In the aforementioned manner, each test zone 230-235 has a different reagent. It is to be appreciated that each test zone can alternatively have a different concentration of the same reagent to measure different levels of a single bioassay.

Auxiliary information or identifying text (for example, GL, TG, HbA1C, HDL, TC labels; manufacturer name and date; etc.) that indicates the type of test in each test zone 230-235 can be printed outside and adjacent to the test zones or regions (i.e. auxiliary information area 228). Auxiliary information or identifying text (for example, GL represents glucose, TG represents triglyceride, A1C represents hemoglobin, HDL represents HDL cholesterol, and TC represents total cholesterol) labels the type of test in each test zone 230-235 and can be printed outside and adjacent to the test zones or regions (i.e. reference regions).

The optional filter membrane layer 212 can have a separation membrane 217 (i.e. plasma separation) that covers the total test area 210. Alternatively the optional filter membrane 217 can have a partial separation membrane and partial "other materials" (i.e. paper) to enable the controlled flow of the test sample. The plasma separation membrane 217 can include a series of pores on the top surface as well as the bottom surface. The series of pores can have a pore sized gradient between the top surface and the bottom surface. In particular, the pore size on the top surface can be greater than the pore size on the bottom surface.

Figure 5:
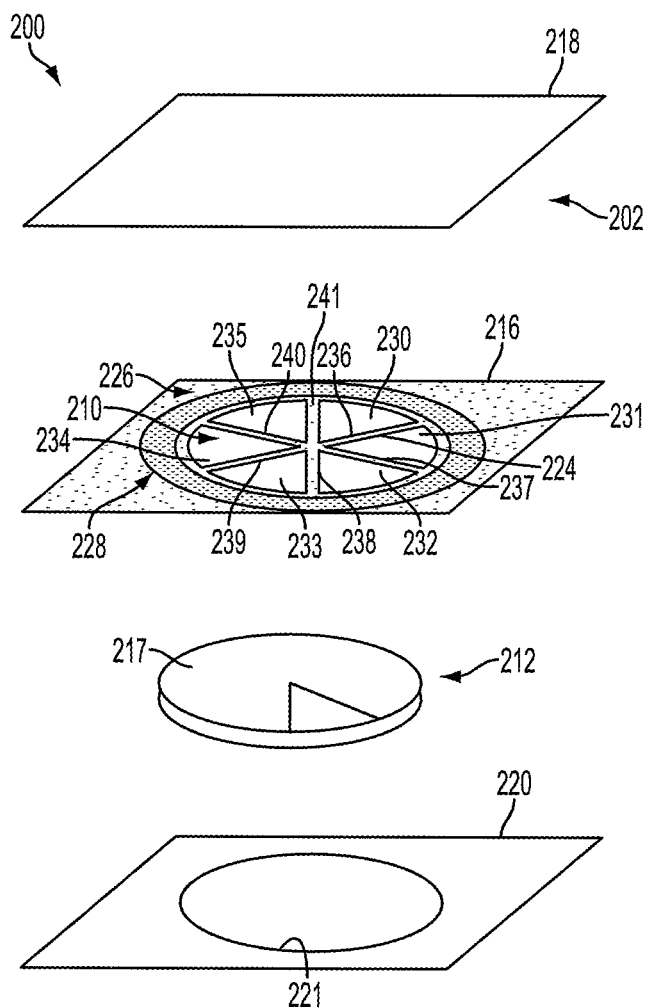
FIG. 5 is an exploded view of a paper based sensor according to the present disclosure.

Membrane layer 212 and structural forming layer 216 can be sandwiched between laminate film layers 218, 220. A hole 221 that is smaller than the size of the membrane 217 can be cut in the bottom lamination layer 220 at the backside of the device (FIG. 5). The plasma separation membrane 217 is visible on the backside of the device 200 when the device 200 is in the assembled arrangement.

Referring again to FIG. 5, the present disclosure proposes a design of a biomedical paper sensor 200 which can determine the concentration of biological materials in fluids such as blood, urine, and saliva. The sensor 200 can contain axially radiating and/or axially symmetric test zones 230-235 arranged similar to slices of a pie (for example) divided by wax ink barriers 236-241 formed by a process that produces thin walls. Each test zone 230-235 can contain a unique test reagent and is identified by printed text (not shown) in area 228. The region 226 of the device outside of the test zone 230-235 can be printed with a uniform reference color. Additionally, the color of the wax wall can also serve as a reference color when it is not clear. Benefits of the sensor 200 include increased accuracy in the measurement of the concentration of biological materials due to the larger area of the test zones. Benefits also include the integration of the reference or calibration color 226 into the sensor 200 which simplifies a visual calibration review, check, or comparison for quantification of the concentration of the test fluid (i.e. test sample).

Figure 6:
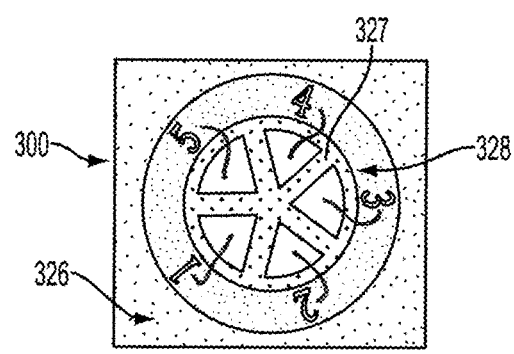
FIG. 6 is an exemplary Triglyceride test paper sensor.

Referring now to FIG. 6, wherein an exemplary Triglyceride paper sensor 300 is therein displayed. Identifying a reference or calibration color area can include a substrate region 328 between the test zones 1, 2, 3, 4, 5 and a calibration color area or region 326. Areas 326, 327, and 328 can be used as reference color areas or contrast color areas. Areas 327 and 328 can be any color to provide contrast (black, color, contrast color, etc.) between the test zones 1-5 and reference areas 326, 327, and 328. It is to be appreciated that the calibration reference area 326 can be separated into multiple sub-areas including separate reference colors associated with each sub-area (not shown). The multiple color reference areas enable use of reagents with different dye colors in test zones 1-5. Alternatively, the reference region can include a first calibration color area including a first predeterminable color for comparing to one or more of the axial test zones. The reference region can further include a second calibration color area including a second predeterminable color for comparing to one or more of the axial test zones. The first and second calibration color areas can each include first and second predeterminable colors, respectively, for comparing to one or more of the axial test zones to report or indicate the concentration of at least two test substance analytes based on the calibrated reading in each test area. In one embodiment, the substrate region 328 can include a contrasting color to distinguish between the test zones 1-5 and the calibration color area 326. Although not shown in FIG. 6, the Triglyceride paper sensor 300 can display a gradient of color change in the test zones 1-5 due to different concentrations of the Triglyceride. The color change or color shade of test zones 1-5 can be compared to the reference color 326 (i.e. magenta). It is to be appreciated that the color change or color density represents the concentration of Triglyceride (for example) from associated test zones 1, 2, 3, 4, 5 and can include concentrations of 100, 150, 200, 250, 300 mg/dL, respectively.

Figure 7:
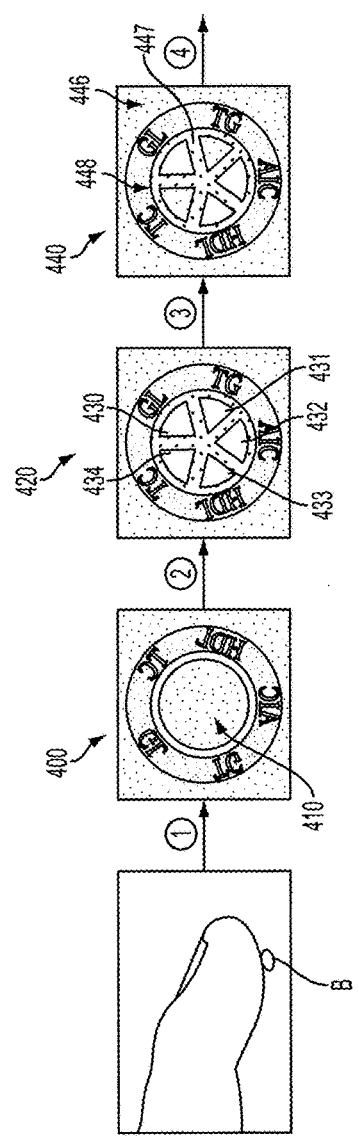
FIG. 7 is a representative display of the paper sensor device and a depiction of a method for using.

FIG. 7 displays a method of using a paper sensor device 400. A blood sample B is taken from a patient or user and placed or 'sucked' into the bottom of the device, i.e. the test area 410, of the paper sensor 400 (step 1). The paper sensor 400 can be turned right side up wherein the blood sample processing can be viewed 420 (step 2). The assay development proceeds in which the blood sample B makes contact with the respective reagents in the test zones 430, 431, 432, 433, 434 (step 3). After the sample has reacted to the reagents, the developed assay is subsequently formed 440 (step 4). Identifying a reference or calibration color area can include substrate regions 447 and 448 between the test zones 430-434 and a calibration color area or region 446. The substrate regions 447 and 448 can include contrasting colors to distinguish between the test zones 430-434 and the calibration color area 446. In the example shown in FIG. 7, the paper sensor 400 can display a gradient of color change in the test zones 430-434 due to different types of reagents, and/or different concentrations of a reagent, that can measure different levels of a bioassay. It is to be appreciated, that each type of analyte (GL, TG, HbA1C, HDL, TC) can be a different reagent, and each analyte/reagent pair can have an associated calibration curve for color reference. Additionally, for a single analyte assay determination, color change in the test zones 430-434 can be due to different concentrations of the same reagent in each test zone. The test zones 430-434 can be compared to the calibration or reference color 446 (i.e. magenta). In this manner, the biomedical paper sensor 400 is used for determining a concentration of biological materials contained in fluids (i.e. blood sample).

As discussed, paper based sensors offer advantages over traditional test strips in terms of cost and multiplexing. The concern of poor accuracy on paper based sensors and test strips, due to colorimetric measurements, has limited them from quantitative applications. In existing test strip applications, a user has to manually compare resultant colors to a set of colors on a reference card. Phone 'apps' can be used to automate the test strip reading process by utilizing the associated phone camera. But the different types and models of cameras, along with the various lighting conditions, presents a challenge to obtain accurate colorimetric measurements.

Traditional test strips require users to manually measure the color with a reference color card, which is unreliable and limits their application in quantitative measurement. Software has been developed which automates the test strip measurement process with the use of phone cameras. The process includes a reference color card which can be used to calibrate the phone camera (for example) red-green-blue (RGB) space and the total intensity can be used for concentration measurements.

The present disclosure provides a colorimetric processing method that can take advantage of a sensor design and does not rely on total intensity as the concentration measurement. The unique sensor design can include two features: a reference color that is printed directly on the paper sensor as a part of the wax channels by a wax printer; and, the reference color and dye colors used in colorimetric reaction are matched in terms of their near-zero absorption in a specific spectral range (e.g. red, green, blue).

Figure 8:
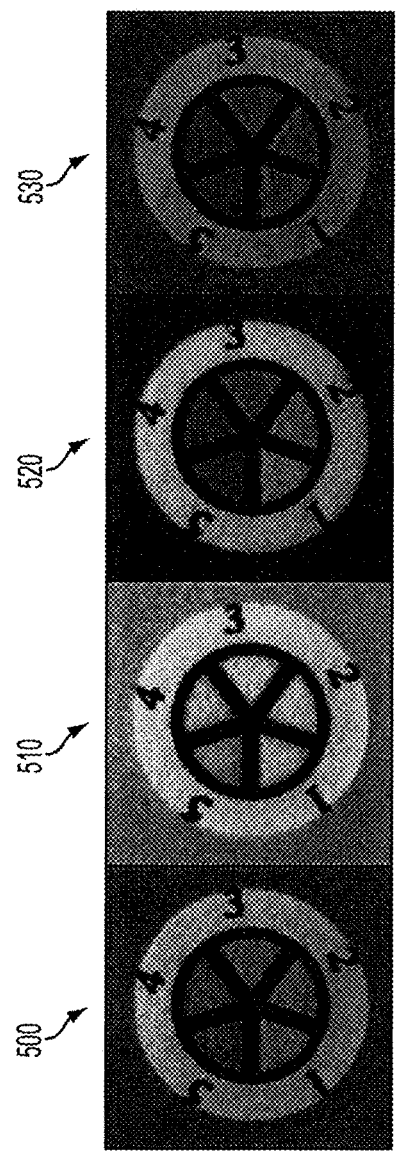
FIG. 8 represents a plurality of sensor images from a first phone camera including its associated red, green, and blue channels or spectral ranges.

The processing method can divide color information into two parts: near-zero absorption part and absorption part, and then use near-zero absorption channel to normalize absorption channels. The method includes the following: taking a picture of vendor or source specific colorimetric paper sensors; the vendor specific paper sensors can include a design wherein the reference color and dye can have little or near-zero absorption in at least one channel for colorimetric reaction; identifying the type of paper sensor by image processing (i.e. text, code, pattern); identifying one color channel in which both dye and reference color have near-zero absorption and the color channels in which both dye and reference color have absorption; acquiring or identifying the known absorption ratio between the dye and the reference color in each channel; locating the test areas in the near-zero absorption channel by image processing (i.e. template matching, feature recognition); separating each test area in full channel from the non-test areas; normalizing each absorption channel by the near-zero absorption channel to remove spatial variation (i.e. paper variation, lighting variation, tint due to deposited chemicals); selectively using additional camera information and/or predetermined weights to construct the composite image from one or more absorption channel; calibrating the test area reading with reference color and substrate white in composite image. The reference color or region can include one or more calibration color areas having predeterminable colors for comparing to one or more of the test areas or zones for reporting or indicating the concentration of test substance (analyte) based on calibrated reading in each test area. In one exemplary arrangement, the calibration color area can include multiple sections. Each section can have a distinct predeterminable color used for a specific analyte. For example, two calibration color sections can comprise one red section and one blue section. In one exemplary arrangement, the red section can be used to calibrate HbA1C and the blue section can be used to calibrate HDL. The aforementioned method has been demonstrated on a paper sensor with different cameras and different lighting conditions. FIG. 8 displays an exemplary paper sensor for a triglyceride test. The sensor image 500 displays a total RGB sensor image produced from a phone camera (i.e. first phone camera). Image 510 represents a sensor image from the phone camera and its associated red channel spectral range. Image 520 represents a sensor image from the phone camera and its associated green channel spectral range. Image 530 represents a sensor image from the phone camera and its associated blue channel spectral range. It is to be appreciated that both the dye and the reference color can show minimized absorption in the red channel 510.

Figure 9:
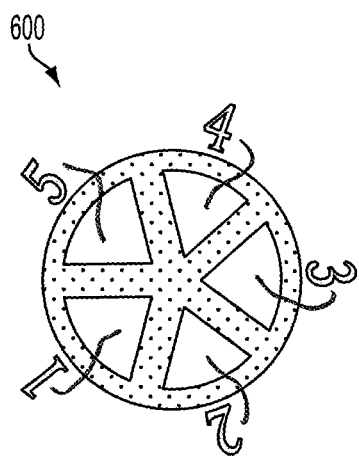
FIG. 9 is a binary image from a red channel that can be used to find the test areas.
Figure 10:
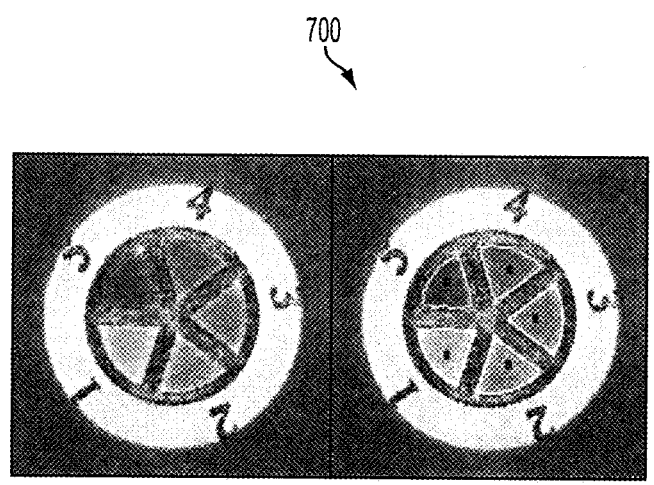
FIG. 10 is a normalized image (blue channel normalized by red channel) and its associated segmented test area.

As shown in FIG. 9, a binary image 600 can be used from the red channel to locate the test areas. Further, as shown in FIG. 10, a near-zero absorption channel can be used to normalize an image 700 (i.e. blue channel normalized by red channel) and its segmented test areas. The normalized image then enables construction of a resultant composite image. It is to be appreciated, that another or second phone camera can capture nearly the identical sensor image (after normalizing) wherein a composite image displays consistent concentrations of test substances. As shown in FIG. 11, a sensor image from a second phone camera shows a total RGB channel 800, its associated red channel 810 spectral range, its associated green channel 820 spectral range, and its associate blue channel 830 spectral range.

As shown in FIG. 12, the exemplary readings from two separate cameras thus display nearly identical images. When plotted, similar triglyceride concentration levels are processed from the two separate camera readings. FIG. 12 displays the triglyceride concentrations of respective test zones 1, 2, 3, 4, 5 from the sensor images 500, 800 respectively. FIG. 12 plots the resultant signals relative to triglyceride concentrations plotting the processed camera readings from the first phone camera 500 and the second phone camera 800.

The present disclosure proposes a colorimetric method that couples sensor design with image processing to enable automated evaluation of test results obtained by paper-based sensors. The proposed method can match ink color and dye used in colorimetric reaction in terms of their absorption in spectral ranges (e.g., red, green, blue). The near-zero absorption channel is then used to normalize absorption channels and construct a composite image. A normalized image can be extracted by normalizing the blue channel by the red channel with given information about the absorption ratio of reference color in both blue and red channels. Benefits of the invention include enabling an automated method to evaluate test results obtained by paper based sensors.

Some portions of the detailed description herein are presented in terms of algorithms and symbolic representations of operations on data bits performed by conventional computer components, including a central processing unit (CPU), memory storage devices for the CPU, and connected display devices. These algorithmic descriptions and representations are the means used by those skilled in the data processing arts to most effectively convey the substance of their work to others skilled in the art. An algorithm is generally perceived as a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be understood, however, that all of these and similar terms are to be associated with the appropriate physical quantities and are merely convenient labels applied to these quantities. Unless specifically stated otherwise, as apparent from the discussion herein, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The exemplary embodiment also relates to an apparatus for performing the operations discussed herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and displays presented herein are not inherently related to any particular computer or other apparatus. Various general-purpose systems may be used with programs in accordance with the teachings herein, or it may prove convenient to construct more specialized apparatus to perform the methods described herein. The structure for a variety of these systems is apparent from the description above. In addition, the exemplary embodiment is not described with reference to any particular programming language. It will be appreciated that a variety of programming languages may be used to implement the teachings of the exemplary embodiment as described herein.

A machine-readable medium includes any mechanism for storing or transmitting information in a form readable by a machine (e.g., a computer). For instance, a machine-readable medium includes read only memory ("ROM"); random access memory ("RAM"); magnetic disk storage media; optical storage media; flash memory devices; and electrical, optical, acoustical or other form of propagated signals (e.g., carrier waves, infrared signals, digital signals, etc.), just to mention a few examples.

The methods illustrated throughout the specification, may be implemented in a computer program product that may be executed on a computer. The computer program product may comprise a non-transitory computer-readable recording medium on which a control program is recorded, such as a disk, hard drive, or the like. Common forms of non-transitory computer-readable media include, for example, floppy disks, flexible disks, hard disks, magnetic tape, or any other magnetic storage medium, CD-ROM, DVD, or any other optical medium, a RAM, a PROM, an EPROM, a FLASH-EPROM, or other memory chip or cartridge, or any other tangible medium from which a computer can read and use.

Alternatively, the method may be implemented in transitory media, such as a transmittable carrier wave in which the control program is embodied as a data signal using transmission media, such as acoustic or light waves, such as those generated during radio wave and infrared data communications, and the like.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

The present disclosure proposes a new colorimetric process method that combines both sensor design and image processing to achieve robust and accurate result readings from paper based sensors with various different cameras and/or under various different lighting conditions. Unlike the test strip application where a color reference card is required, a print reference color can be incorporated along with hydrophobic channels on a paper sensor substrate during device fabrication. Importantly, the present disclosure provides a method for matching ink color and dye used in colorimetric reaction in terms of their absorption in a specific spectral range (e.g. red, blue). The process further uses near-zero absorption channels to normalize absorption channels and construct a composite image. The reading can be further calibrated with known reference ink colors and substrate white. This invention provides the user with real-time quantitative results.

What is claimed is:

1. A colorimetric processing method for paper based sensors, comprising:
   using a camera and taking a picture of a colorimetric paper sensor for colorimetric reactions;
   identifying the type of paper sensor by image processing;
   identifying one color channel in which both a dye and reference color have near zero absorption and wherein the color channels in which both the dye and the reference color have absorption;
   identifying the known absorption ratio between the dye and the reference color in each color channel;
   separating each test area in the channel from the non-test areas;
   normalizing each absorption channel by the near zero absorption channel to remove spatial variation;
   calibrating the test area reading with the reference color and a substrate white in the composite image; and,
   reporting the concentration of a test substance analyte based on the calibrated reading in each test area.

2. The method according to claim 1, further comprising:
   locating the test areas in the near zero absorption channels by image processing.

3. The method according to claim 2, further comprising:
   using an additional camera and taking another picture of the colorimetric paper sensor to construct a composite image from one or more absorption channels.

4. The method according to claim 1, wherein the colorimetric paper sensor is a biomedical paper sensor for determining a concentration of biological materials in fluids comprising:
   a plurality of axial symmetric test zones;
   wherein the test zones radiate outward from a central point;
   each of the axial symmetric test zones divided by wax ink barrier walls;
   each of the axial symmetric test zones contain a unique test reagent therein;
   a reference region surrounding the plurality of axial test zones; and,
   wherein the reference region includes a first calibration color area including a first predeterminable color for comparing to one or more of the axial test zones.

5. The method according to claim 4, wherein the plurality of test zones is at least two.

6. The method according to claim 4, wherein the biomedical paper sensor further comprises:
   a total device area including the combined areas of a reference region area and the axial test zones area; and,
   wherein the axial test zones area is at least 37.5% of the total device area.

7. The method according to claim 4, wherein an area of each of the axial symmetric test zones is at least 5 mm$^2$.

8. The method according to claim 4, wherein the wax ink barrier walls include a thickness of at least 100 μm.

9. The method according to claim 6, wherein the reference region area further includes a substrate region separating the axial test zones area and the calibration color area.

10. The method according to claim 4, wherein the reference region further includes a second calibration color area including a second predeterminable color for comparing to one or more of the axial test zones; and,
    wherein the first and second calibration color areas each include first and second predeterminable colors, respectively, for comparing to one or more of the axial test zones to report the concentration of at least two test substance analytes based on the calibrated reading in each test area.

11. A colorimetric processing method for paper based sensors, comprising:
    taking a picture of a colorimetric paper sensor for colorimetric reactions;
    identifying the type of paper sensor by image processing;
    identifying one color channel in which both a dye and reference color have near zero absorption and wherein the color channels in which both the dye and the reference color have absorption;
    identifying the known absorption ratio between the dye and the reference color in each color channel;
    separating each test area in the channel from the non-test areas;
    normalizing each absorption channel by the near zero absorption channel to remove spatial variation;
    wherein the colorimetric paper sensor is a biomedical paper sensor;
    wherein the paper sensor includes a plurality of axially radiating test zones;
    each of the axially radiating test zones divided by wax ink barrier walls;
    each of the axially radiating test zones contain a unique test reagent therein;
    a reference region surrounding the plurality of axially radiating test zones; and,
    wherein the reference region includes a calibration color area including a predeterminable color for comparing to one or more of the axially radiating test zones.

12. The method according to claim 11, wherein the paper sensor includes:
    a total device area including the combined areas of a reference region area and the axially radiating test zones area; and,
    wherein the axially radiating test zones area is at least 37.5% of the total device area.

13. The method according to claim 12, wherein the reference region area further includes a substrate region separating the axially radiating test zones area and the calibration color area.

14. A colorimetric processing method for paper based sensors, comprising:
    taking a picture of a colorimetric paper sensor for colorimetric reactions;
    identifying the type of paper sensor by image processing;
    identifying one color channel in which both a dye and reference color have near zero absorption and wherein the color channels in which both the dye and the reference color have absorption;

identifying the known absorption ratio between the dye and the reference color in each color channel;
separating each test area in the channel from the non-test areas;
normalizing each absorption channel by the near zero absorption channel to remove spatial variation;
wherein the colorimetric paper sensor is a biomedical paper sensor;
wherein the paper sensor includes a plurality of axially radiating test zones;
each of the axially radiating test zones divided by wax ink barrier walls;
each of the axially radiating test zones contain a unique test reagent therein;
a reference region surrounding the plurality of axially radiating test zones;
a total device area including the combined areas of a reference region area and the axially radiating test zones area;
wherein the axially radiating test zones area is at least 37.5% of the total device area; and,
wherein the reference region area further includes a substrate region separating the axially radiating test zones area and the calibration color area.

15. The method of claim 14, wherein the reference region includes a calibration color area including a predeterminable color for comparing to one or more of the axially radiating test zones.

16. A colorimetric processing method for paper based sensors, comprising:
taking a picture of a colorimetric paper sensor for colorimetric reactions;
identifying the type of paper sensor by image processing;
identifying one color channel in which both a dye and reference color have near zero absorption and wherein the color channels in which both the dye and the reference color have absorption;
identifying the known absorption ratio between the dye and the reference color in each color channel;
separating each test area in the channel from the non-test areas;
normalizing each absorption channel by the near zero absorption channel to remove spatial variation; and,
wherein the colorimetric paper sensor is a biomedical paper sensor.

17. The method according to claim 16, wherein a number of test areas is at least two.

18. The method according to claim 16, wherein the biomedical paper sensor further comprises:
a total device area including the combined areas of a reference region area and the axial test zones area; and,
wherein the axial test zones area is at least 37.5% of the total device area.

19. The method of claim 16, wherein the paper sensor includes a structural forming layer having a reference region surrounding a plurality of axially radiating test zones; and,
wherein said reference region includes a calibration color area including a predeterminable color for comparing to one or more of the plurality of axially radiating test zones.

20. The method of claim 19, wherein said reference region includes another calibration color area including a predeterminable color for comparing to one or more of the plurality of axially radiating test zones.

21. The method of claim 20, further comprising:
using an additional camera and taking another picture of the colorimetric paper sensor to construct a composite image from one or more absorption channels.

* * * * *